United States Patent [19]

Nelson et al.

[11] Patent Number: 4,659,330
[45] Date of Patent: Apr. 21, 1987

[54] HYPODERMIC SYRINGE NEEDLE GUARD

[76] Inventors: Robert Nelson, 14661 Gault St., Van Nuys, Calif. 91405; Robert Flome, 15805 St. Timothy Rd., Apple Valley, Calif. 92307

[21] Appl. No.: 796,280

[22] Filed: Nov. 8, 1985

[51] Int. Cl.⁴ .............................................. A61M 5/32
[52] U.S. Cl. ................................... 604/192; 604/263
[58] Field of Search ............................... 604/192, 263

[56] References Cited
FOREIGN PATENT DOCUMENTS
1240228  5/1967  Fed. Rep. of Germany ...... 604/192

OTHER PUBLICATIONS
European Patent Application, 0160849, Filed Apr. 9, 1984.

Primary Examiner—John D. Yasko

[57] ABSTRACT

A guard for a hypodermic syringe needle which keeps the extremities and particularly the hands well away from the syringe to prevent accidental punctures with contaminated needles. The needle guard is in the form of a cylindrical cap which slides over the needle having a manipulating device to remove and replace the guard while keeping the hands well away from the needle. In one embodiment the manipulating device is in the form of a flexible handle having a resilient clamping flanges which clamp the device around the barrel of the syringe. The extension has a webbed hinge allowing it to easily flex outward away from the syringe needle for removal or replacement of the end cap. Alternately the end cap may be hingedly attached to a collar slideable on the syringe barrel by which the cap can be slid downward to remove the cap and retracted to replace the cap. The needle guard may also be in the form of a second cylinder forming a slideably mounted sleeve on the syringe barrel to cover the needle when extended or expose the needle when retracted.

5 Claims, 15 Drawing Figures

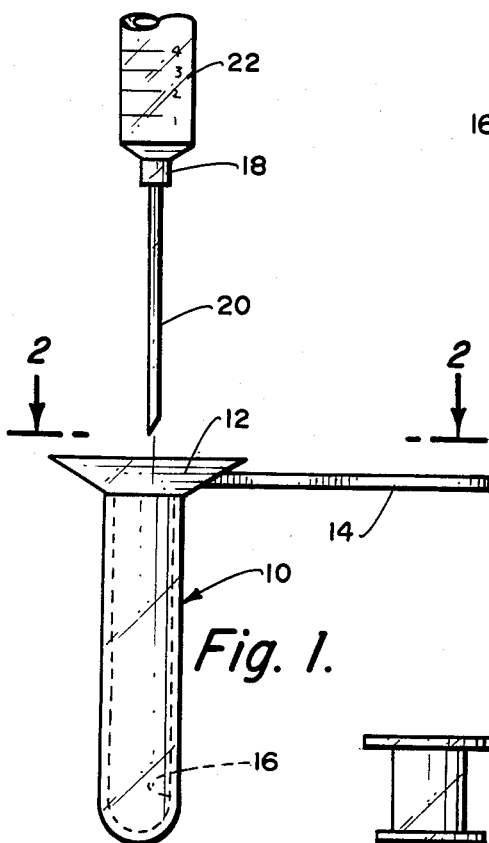
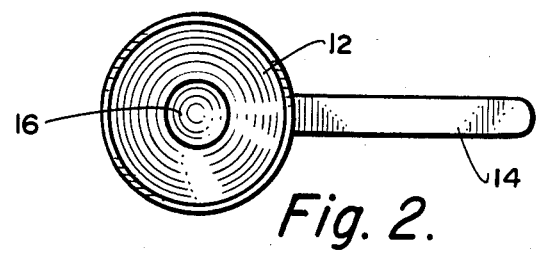
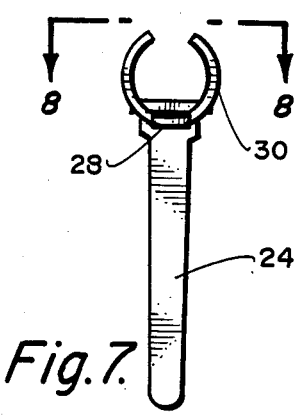
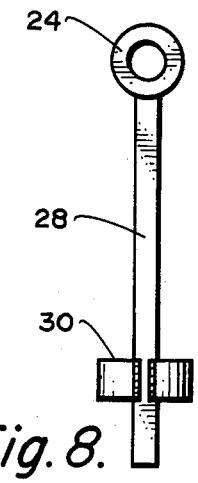
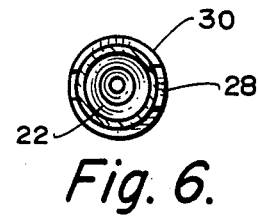
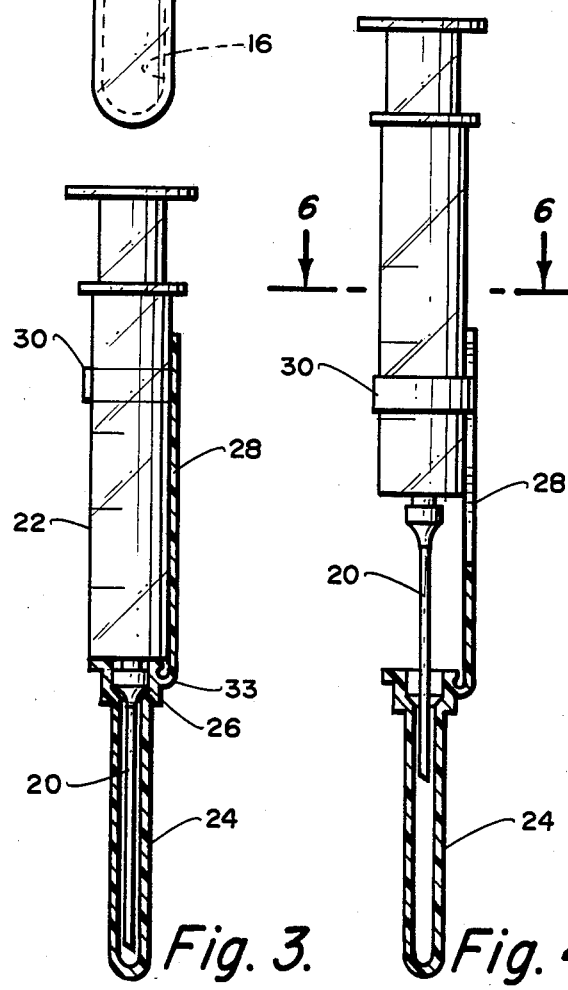
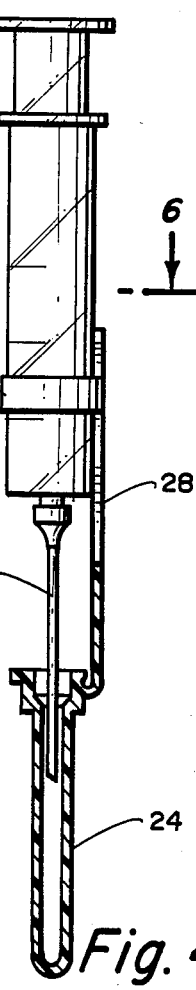
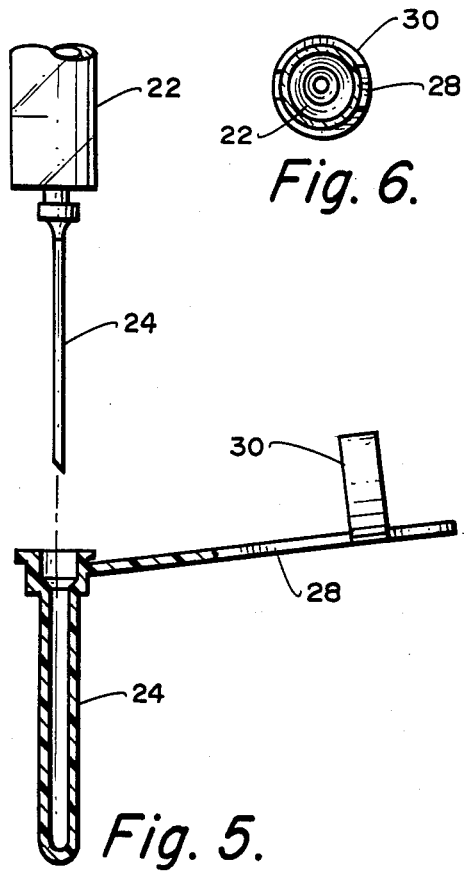

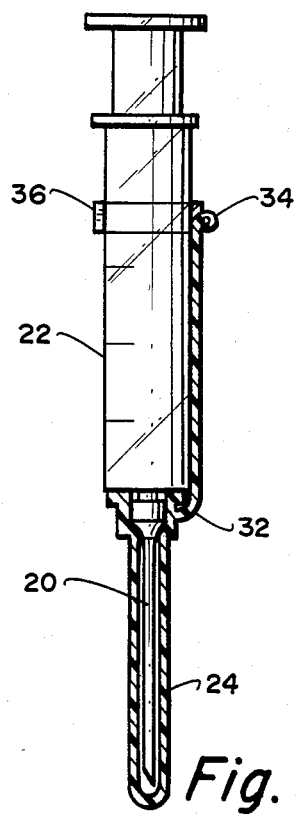
Fig. 9.
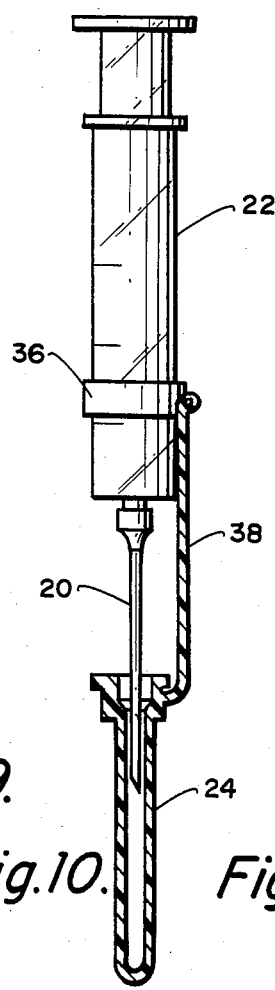
Fig. 10.
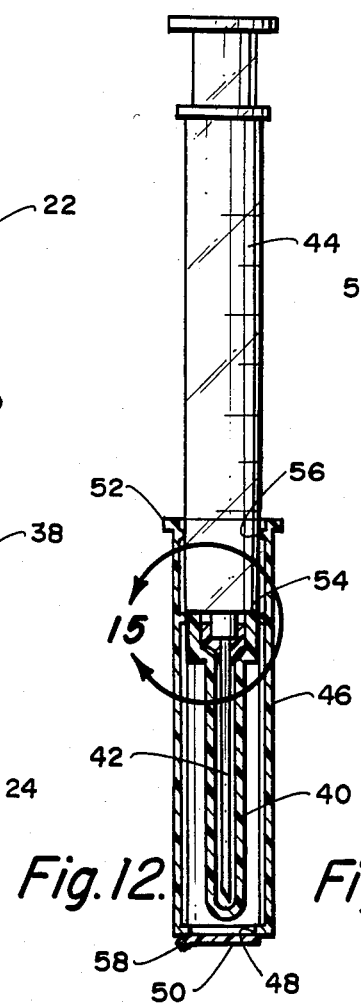
Fig. 12.
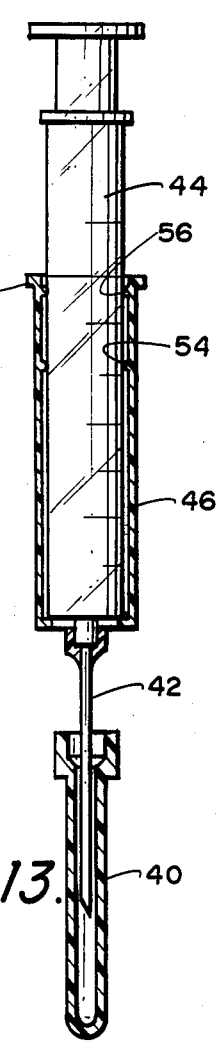
Fig. 13.
Fig. 14.
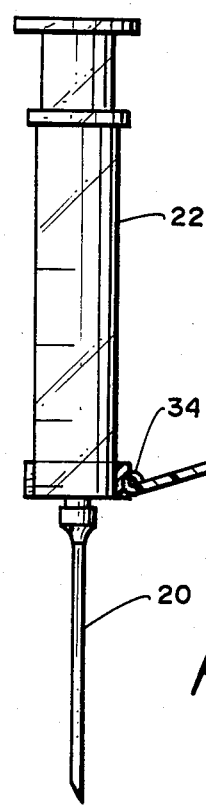
Fig. 11.
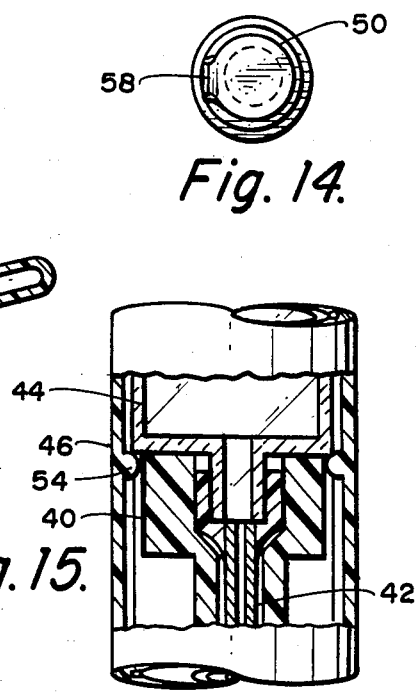
Fig. 15.

4,659,330

HYPODERMIC SYRINGE NEEDLE GUARD

FIELD OF THE INVENTION

This invention relates to hypodermic syringes and more particularly relates to methods to prevent accidental puncture with contaminated needles on hypodermic syringes.

BACKGROUND OF THE INVENTION

Hypodermic syringes of known constructions employ a cylindrical barrel having a needle covered with an end cap. To use the syringe, the end cap is slipped off and the needle inserted into a patient to inject a fluid with a plunger or aspirate blood and other bodily fluids back into the syringe. After use the cap is replaced on the needle and both are discarded. A not infrequent problem with these devices however is the accidental puncture of the medical attendant using the syringe when replacing the cap. Often this occurs when the cap is being replaced and requires care to be sure the needle is properly inserted in the cap. If a distraction occurs the user can easily miss the entrance to the cap and puncture the finger or some other portion of the hand or arm. Since these needles are frequently used on patients that have serious blood borne diseases the contamination can be transferred to the medical attendant infecting them with the disease of the patient. This can have serious side affects if the disease is an infectious disease such as hepatitis, aids or other infectious diseases. It would be advantageous if some method could be provided for replacement of a protective cap on the needle while keeping the extremities and particularly the hands well away from the needle point.

Examples of caps for hypodermic syringe needles are shown in U.S. Pat. Nos. 2,408,323, 2,571,653, 3,073,306, 3,527,216, 3,890,971, 4,355,822, 4,373,526 and 4,425,120, all show a slideable shield to protect the needle on a hypodermic syringe. Each of these devices is quite complex and requires special manufacture of the hypodermic syringe. To date none of these devices appear to be on the market for reasons which should be apparent from an examination of the patents. U.S. Pat. Nos. 3,825,003, 3,976,069 and 4,249,530 all show caps which act as needle guards. None of the devices appear to show a simple, easy to manufacture protective cap which can be used with existing syringes and needles.

SUMMARY OF THE INVENTION

The purpose of the present invention is to provide a protective cap or covering for the needle of a hypodermic syringes to prevent infection from accidental punctures of medical personnel using the syringe.

The purpose of the present invention is to provide the above features in the simplest, most economical manner with a device substantially adaptable to existing syringes and needles. In one embodiment the usual end cap fitted over the hypodermic needle has an arm extension for removing and replacing the cap. In a modified version deformable clips which snaps around the on the end of the arm either partially or wholly snaps cylindrical body of the hypodermic syringe. The clips may easily slide on the syringe body allowing the cap to be pushed downward or outward away from the needle. Alternatively the clips may be sapped off the body allowing the arm extension to be used as a convenient handle to hold the cap entrance away from the fingers.

Alternatively the end cap could be connected in such a way that when the needle is free of the end cap the end cap can be pivoted away from the needle and the extension with the clips retracted on the syringe body allowing the needle to be freely used. The syringe may now be used in the usual fashion of injecting the needle and discharging the contents of the syringe through the needle. Additionally the needle and end cap may be removed from the syringe and discarded if medical personnel are to perform an arterial blood gas procedure that requires the removal of the needle from the syringe to facilitate introduction of a blood sample into a blood gas analyzer.

The end cap is hinged either at the joint between the extension and the cap or could be hinged at the clips. In the former the clips would only pass partially around the barrel of the syringe so that they could be easily snapped off the syringe to remove the end cap totally. Another alternative has the hinge at the a collar permanently retained on the syringe instead of clips so that the end cap is always kept attached to the syringe to prevent the cap from being misplaced. In the latter embodiment the collar is slid along the barrel of the syringe until the end cap is clear of the end of the needle and then along with the extension is allowed to swing away from the needle. The needle may now be used in the usual manner.

As a further alternative, a slideable sheath or sleeve could be provided which slips over existing syringes and protective end caps which remains in an extended position until ready for use. The sleeve is then slid back to expose the protective end cap which can be pulled off and discarded or put back in place if desired. The syringe may now be used and after use the sleeve extended to cover and protect against any punctures from an exposed contaminated needle with the cap replaced if desired. The advantage of the latter design is that the sleeve can be simply provided as an accessory to existing syringes which simply slides over and snaps onto the syringe barrel or cylinder. A tear-off protective cover closes the end of the sleeve. This seals the entire area around the needle and protective end cap. Preferably the sleeve is adaptable to existing, in use syringes with end caps while at the same time providing the medical attendant or user from protection against a puncture with a contaminated needle. Thus in each of the embodiments described above these features are met with a simplicity of design which minimizes their cost while maximizing their convenience and protection.

It is therefore one object of the present invention to provide a hypodermic syringe needle guard which is simple in construction and easy to use.

Yet another object of the present invention is to provide a needle guard which does not deviate substantially from existing technology for needle protection. Instead it uses the existing technology to provide a needle guard by adapting generally used needle guards for protection by adding a small feature or adding a part which does not modify the existing structure.

The above and other features of the invention will be more fully understood from the following detailed description and the accompanying drawings, in which:

BRIEF DESCRIPTION OF THE DRAWINGS

FIG. 1 is a side elevation of a very simple cap protection device according to the invention.

FIG. 2 is a view taken at 2—2 of FIG. 1.

FIG. 3 is a alternate embodiment of the invention in which an extension on the end cap is secured to the syringe body.

FIGS. 4 and 5 illustrate removal of the protective end cap of the embodiment of FIG. 3.

FIG. 6 is a sectional view taken at 6—6 of FIG. 4.

FIG. 7 is a side elevation of the end cap arm extension, and clip of FIG. 5.

FIG. 8 is a top elevational view taken at 8—8 of FIG. 7.

FIG. 9 is a further embodiment of the invention showing the protective end cap secured to the syringe body.

FIGS. 10 and 11 illustrates the operation of the device of FIG. 9.

FIG. 12 illustrates yet another embodiment of the invention including a slideable protectable sleeve in conjunction with protective end cap.

FIG. 13 illustrates the operation of the device of FIG. 12.

FIG. 14 is a bottom view of the embodiment of FIG. 12

FIG. 15 is a detailed sectional view taken at 15 of FIG. 12.

DETAILED DESCRIPTION OF THE INVENTION

The simplest form of protection for a needle guard is illustrated in FIGS. 1 and 2. In this embodiment the protective end cap is in the form of an elongated cap 10 having a funnel shaped collar 12 and arm extension 14. Cap 10 has a hollow interior at 16 which tightly fits neck 18 at the upper end of needle 20.

Medical personnel using the hypodermic syringe grasps arm extension 14 or cap 10 to pull the protective cap away from needle 20 exposing the needle for use. After use the cap is replaced by holding extension 14 so that funnel shaped collar 12 prevents mishaps by assuring that the end of needle 20 is guided into cavity 16 in the cap.

The embodiment in FIG. 1 is simple in construction but has the disadvantage that arm extension or handle 14 extends outward from the cap making, packaging, shipping and storing a problem. To avoid this problem the embodiment of FIGS. 3 through 8 was conceived. In this embodiment cap 24 is provided to cover needle 20 attached to body 22 of the syringe. Cap 24 is held in place by a tight frictional fit at 26 and also by the arm or handle 28 having deformable spring clips 30 formed on the end of handle 28. A hinge 32 is formed on arm extension 28 at the point where it joins cap 24.

An advantage of this construction is that the cap may be easily removed by sliding the cap downward with a push on clips 30 forcing handle 28 downward until cap 24 is clear of needle 20. Clips 30 may now be snapped off from around body 22 of the syringe freeing the syringe for use.

Alternatively, clips 30 can be pushed downward on syringe body 22 to very near the end or until cap 24 clears the end of the needle allowing the cap to swing outward perpendicular to the needle. Clips 30 can then be slid upward on the syringe body 22 keeping the protective cap and handle 28 firmly attached to the syringe so that it may not be misplaced.

To facilitate the latter arrangement, the embodiment of FIGS. 9 through 11 is provided. In this embodiment end cap 24 is is attached to arm extension 38 by hinge 32 as before but an additional pinned hinge 34 is provided attached to collar 36 mounted on cylindrical body 22. The structure is substantially the same as the embodiment of FIGS. 3 through 8 except that with collar 36, the protective end cap remains with the syringe until discarded. In use collar 36 and arm 38 are slid down on syringe body 22 until end cap 24 clears the end of needle 20 as shown in FIG. 11. Cap 24 may then be swung up and away from the needle. The needle and syringe are now free for use. To replace the cap the procedure is simply reversed. Protective end cap 24 is swung down into position below the needle and collar 36 pulled backward with the fingers on body 22 of the syringe drawing cap 24 into the position shown in FIG. 9 over the needle. The advantage of this type of construction is that the hands never need be placed at a position adjacent to or beyond the sharp, pointed end of needle 20, therefore, the possibility of medical personnel to get stuck by a contaminated needle is minimized or eliminated. Alternatively if desired cap 24 can be attached to need le 20 and the ientire protective end cap assembly removed by twisting or pulling down on the cap until collar 36 clears syringe body 22.

Another embodiment which utilizes the principals of the embodiment of FIGS. 9 through 11 is illustrated in FIGS. 12 through 15. The advantage of this embodiment is that it can be adapted to a standard syringe having a snap-on protective end cap 40 covering needle 42 attached to standard syringe body 44 of a hypodermic syringe. The cap 40 is a simple pull-off type cap supplied with standard hypodermic disposal syringes. To this configuration is added sleeve 46 having opening 48 covered by a adhesive secured membrane 50 as can be seen more clearly in FIG. 14. The sleeve 46 is a simple hollow cylinder having a gripping flange 52 at the upper end and aperture 48 sufficiently large to clear the protective cap 40 when the sleeve 46 is retracted. The sleeve is secured to the cylindrical body 44 of the syringe by a circumferential ribs 54 and 56 on the inside surface of sleeve 46. Upper circumferential rib 56 frictionally retains sleeve 46 on the body 44 while lower rib 54 retains sleeve 46 in an extended position shown in FIG. 12 covering end cap and needle 40 and 42, respectively.

In use sheath or sleeve 46 is drawn back on hypodermic syringe body 44 after removal of protective membrane 50 by pulling tab 58. Protective end cap 40 may now be removed in the usual manner and either discarded or retained for replacement after use if desired.

The needle is now exposed for injection and discharging the contents of the syringe or for withdrawing fluid from a patient. After use, sleeve 46 is slid downward by grasping and pushing downward on flange 52 until rib 54 passes beyond the end of body 44 with the sleeve completely covering and protecting needle 42. Needle cap 40 can be safely inserted through the opening 48 and pushed back on needle 42 if the syringe is to be used in a procedure such as an arterial blood gas analysis.

As can be seen in the last embodiment the sleeve is adaptable to existing syringes by simply inserting the sheath over the existing end cap engaging the body of the syringe. This makes the device very economical to manufacture and adapt to existing syringes having protective needle end caps 40.

This invention is not to be limited by the embodiment shown in the drawings and described in the description which is given by way of example and not of limitation but only in accordance with the scope of the appended claims.

What is claimed is:

1. A hypodermic syringe needle guard comprising;
a hollow tubular cap means having an open end and a closed end fitting over and shielding said needle;
an elongated handle attached to said hollow tubular cap means proximate said open end, said elongate handle being constructed and arrange to extend a substantial distance away from said cap means so that said cap means can be removed and replaced while keeping hands away from said needle;
hinge means hingedly attaching one end of said handle to said tubular cap means;
securing means secruing the free end of said elongate handle remote from said hinge means to said syringe whereby said elongate handle may be secured out of the way on said syringe when said tubular cap is in place on said needle.

2. The needle guard according to claim 1 in which said securing means comprises a pair of clips on the free end of said elongate handle construction to snap on said syringe.

3. The needle guard according to claim 1 in which said securing mens comprises a collar attached to said free end of said handle constructed to slidably secure said free end of said elongate handle on said syringe.

4. The needle guard according to claim 3 including a hinge securing said collar to said free end of said elongate handle whereby said collar may be slid down on said syringe until said tubular cap clears said needle and can be swung away from said needle.

5. The needle according to claim 4 in which the first hinge is a self-hinge and said second hinge is a pinned hinge.

* * * * *